United States Patent
Kumazawa et al.

(10) Patent No.: US 11,504,695 B2
(45) Date of Patent: Nov. 22, 2022

(54) WATER-ABSORBING RESIN

(71) Applicant: SUMITOMO SEIKA CHEMICALS CO., LTD., Hyogo (JP)

(72) Inventors: Kenta Kumazawa, Himeji (JP); Tetsuhiro Hinayama, Himeji (JP); Yohei Yamamoto, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 567 days.

(21) Appl. No.: 16/498,319

(22) PCT Filed: Mar. 22, 2018

(86) PCT No.: PCT/JP2018/011351
§ 371 (c)(1),
(2) Date: Sep. 26, 2019

(87) PCT Pub. No.: WO2018/180864
PCT Pub. Date: Oct. 4, 2018

(65) Prior Publication Data
US 2020/0353442 A1 Nov. 12, 2020

(30) Foreign Application Priority Data
Mar. 29, 2017 (JP) .............................. JP2017-066207

(51) Int. Cl.
*B01J 20/26* (2006.01)
*B01J 20/28* (2006.01)
(Continued)

(52) U.S. Cl.
CPC ............. *B01J 20/261* (2013.01); *A61F 13/53* (2013.01); *B01J 20/28004* (2013.01);
(Continued)

(58) Field of Classification Search
CPC ................ B01J 20/261; B01J 20/28004; B01J 20/28033; B01J 20/28047; B01J 20/3007;
(Continued)

(56) References Cited

U.S. PATENT DOCUMENTS

| 4,542,176 A | * | 9/1985 | Graham | ............. C08G 18/4833 524/556 |
| 6,121,509 A | * | 9/2000 | Ashraf | .................... A61L 15/60 604/372 |

(Continued)

FOREIGN PATENT DOCUMENTS

| EP | 2 752 430 A1 | 7/2014 |
| EP | 2 993 191 A1 | 3/2016 |

(Continued)

OTHER PUBLICATIONS

Extended European Search Report from European Patent Application No. 18777573.9 dated Dec. 15, 2020.
(Continued)

*Primary Examiner* — Joseph D Anthony
(74) *Attorney, Agent, or Firm* — Knobbe, Martens, Olson & Bear, LLP (57) ABSTRACT

Provided is a water-absorbent resin which is capable of giving an absorbent material improved gel-shape stability and which has excellent water-absorption capacity. A water-absorbent resin of the present invention is a polymer of a water-soluble ethylenically unsaturated monomer, and has the following properties (1) and (2): (1) A disintegration amount at 20-fold swelling is 30% by mass or less; and (2) a solubility in physiological saline is 25% by mass or less. (Determination Method for Disintegration Amount at 20-Fold Swelling) 5 g of the water-absorbent resin is added to 100 g of physiological saline to allow the water-absorbent resin to absorb the physiological saline, thereby obtaining a gel. The obtained gel is divided approximately equally into (Continued)

five portions, and these portions are introduced respectively into cylindrical molds having a length of 3.6 cm and a radius of 2.8 cm and molded. The masses of the five molded cylindrical gels are measured. The heaviest and the lightest of the five gels are removed, and the remaining three gels are used as samples. A mass Wa (g) of each sample is measured. Each weighed sample is placed on the uppermost sieve of a combination of JIS standard sieves having a mesh size of 5.6 mm and a receptacle in this order and shaken for 10 minutes using a Ro-Tap shaker (rotation speed, 290 rpm; number of taps, 165 rpm). A mass Wb (g) of the gel which has passed through the sieves is measured. The disintegration amount of each sample is calculated using the following equation: Disintegration amount of sample (%)=Wb (g)/Wa (g)×100. An average of the disintegration amounts for three samples to be measured is regarded as the disintegration amount at 20-fold swelling of the water-absorbent resin.

6 Claims, 1 Drawing Sheet

(51) Int. Cl.
*A61F 13/53* (2006.01)
*B01J 20/30* (2006.01)
*C08F 20/06* (2006.01)

(52) U.S. Cl.
CPC ... *B01J 20/28033* (2013.01); *B01J 20/28047* (2013.01); *B01J 20/3007* (2013.01); *A61F 2013/530299* (2013.01); *A61F 2013/530605* (2013.01); *C08F 20/06* (2013.01)

(58) Field of Classification Search
CPC . B01J 20/26; B01J 20/28; A61F 13/53; A61F 2013/530299; A61F 2013/530605; C08F 20/06; C08F 2810/20; C08F 2/32; C08F 8/14; C08F 20/04; C08F 265/02; A61L 15/24; A61L 15/60
See application file for complete search history.

(56) References Cited

U.S. PATENT DOCUMENTS

| 2005/0181200 | A1* | 8/2005 | Mertens | C08J 3/12 264/109 |
| 2005/0245684 | A1* | 11/2005 | Daniel | A61L 15/24 525/178 |
| 2009/0182092 | A1* | 7/2009 | Yokoyama | C08F 2/18 524/849 |
| 2018/0185820 | A1 | 7/2018 | Tada et al. | |
| 2020/0010461 | A1* | 1/2020 | Parks | A61K 31/496 |

FOREIGN PATENT DOCUMENTS

| EP | 3 029 077 A1 | 6/2016 |
| JP | S63-92701 A | 4/1988 |
| JP | 2009-132755 A | 6/2009 |
| WO | WO 2007-126003 A1 | 11/2007 |
| WO | WO 2016-158975 A1 | 10/2016 |

OTHER PUBLICATIONS

International Search Report in International Application No. PCT/JP2018/180864, dated May 22, 2018.
European Office Action in European Patent Application No. 18777573.9 dated Dec. 10, 2021.

* cited by examiner

WATER-ABSORBING RESIN

TECHNICAL FIELD

The present invention relates to a water-absorbent resin. More specifically, the present invention relates to a water-absorbent resin which is capable of giving an absorbent material improved gel-shape stability and which has excellent water-absorption capacity.

BACKGROUND ART

In recent years, a water-absorbent resin is widely used in various fields including hygienic materials such as disposable diapers and sanitary napkins; agricultural and horticultural materials such as a water-retention agent and a soil conditioner; and industrial materials such as a water blocking agent and a dew condensation prevention agent. Among these fields, the water-absorbent resins are most often used especially for hygienic materials such as disposable diapers and sanitary napkins.

As such water-absorbent resins, there are known, for example, hydrolysates of starch-acrylonitrile graft copolymers, neutralized products of starch-acrylonitrile graft copolymers, saponified products of vinyl acetate-acrylic acid ester copolymers, and crosslinked products of partially neutralized polymers of acrylic acid.

An absorbent article such as a disposable diaper, a sanitary napkin, or an incontinence pad is composed of an absorbent material that absorbs and retains a body liquid such as urine or menses excreted from the body, the absorbent material being positioned mainly in a central portion, a liquid-permeable front sheet (top sheet) positioned on the side of the absorbent article that is brought into contact with the body, and a liquid-permeable rear sheet (back sheet) positioned opposite to the side that is brought into contact with the body. The absorbent material is usually composed of hydrophilic fibers such as pulp and a water-absorbent resin.

The absorbent material temporally retains a liquid having entered through the front sheet with the hydrophilic fibers and then retains the liquid with the water-absorbent resin. Generally, to increase the liquid absorption amount of the absorbent material, it is effective to increase the amount of the water-absorbent resin and thereby relatively reduce the amount of the hydrophilic fibers. However, there is a problem that when the absorbent material has absorbed a liquid, the volume of the absorbent material increases due to swelling of the water-absorbent resin, causing decrease in intertwinement of the fibers themselves or of the water-absorbent resin with the fibers. This problem becomes more remarkable by increasing the amount of the water-absorbent resin and thereby relatively reducing the amount of the hydrophilic fibers. Such decrease in intertwinement of the fibers themselves or of the water-absorbent resin with the fibers becomes a serious drawback in the case of using the water-absorbent material as a hygienic material because when compression or a shearing force is applied to the absorbent material, deformation such as cracking or uneven distribution occurs, and moreover inhibition of liquid absorption or re-wet of a liquid occurs.

As a method for preventing deformation of an absorbent material, there has heretofore been known a method of developing an adhesion force between thermally fused fibers or between pulp and thermally fused fibers by incorporating the thermally fused fibers into the pulp, and thereby improving the gel-shape stability of the absorbent material (see Patent Document 1). The method of Patent Document 1, however, has a problem that the liquid permeation rate and the absorption amount lower because the thermally fused fibers are hydrophobic though the gel-shape stability of an absorbent material is improved.

PRIOR ART DOCUMENT

Patent Document

Patent Document 1: Japanese Patent Laid-open Publication No. 63-92701

SUMMARY OF THE INVENTION

Problems to be Solved by the Invention

The present application has an object to provide a water-absorbent resin which is capable of giving an absorbent material improved gel-shape stability and which has excellent water-absorption capacity.

Means for Solving the Problem

The inventors of the present invention conducted a diligent study to solve the aforementioned problem. As a result, it has been found that in a polymer of a water-soluble ethylenically unsaturated monomer, a disintegration amount at 20-fold swelling and a solubility in physiological saline affect gel-shape stability of an absorbent material and water-absorption capacity of a water-absorbent resin. The present invention has been accomplished as a result of further study based on these findings.

In summary, the present invention provides aspects of the invention comprising the following features:
Item 1. A water-absorbent resin is a polymer of a water-soluble ethylenically unsaturated monomer, and has the following properties (1) and (2):
(1) a disintegration amount at 20-fold swelling is 30% by mass or less; and
(2) a solubility in physiological saline is 25% by mass or less.
(Determination Method for Disintegration Amount at 20-Fold Swelling)

5 g of the water-absorbent resin is added to 100 g of physiological saline to allow the water-absorbent resin to absorb the physiological saline, thereby obtaining a gel. The obtained gel is divided approximately equally into five portions, and these portions are introduced respectively into cylindrical molds having a length of 3.6 cm and a radius of 2.8 cm and molded. The masses of the five molded cylindrical gels are measured. The heaviest and the lightest of the five gels are removed, and the remaining three gels are used as samples. A mass Wa (g) of each sample is measured. Each weighed sample is placed on the uppermost sieve of a combination of JIS standard sieves having a mesh size of 5.6 mm and a receptacle in this order and shaken for 10 minutes using a Ro-Tap shaker (rotation speed, 290 rpm: number of taps, 165 rpm). A mass Wb (g) of the gel which has passed through the sieves is measured. The disintegration amount of each sample is calculated using the following equation:

$$\text{Disintegration amount of sample (\%)} = Wb(g)/Wa(g) \times 100.$$

An average of the disintegration amounts for three samples to be measured is regarded as the disintegration amount at 20-fold swelling of the water-absorbent resin.

Item 2. The water-absorbent resin according to item 1, wherein a median particle diameter is 200 μm to 600 μm.

Item 3. The water-absorbent resin according to item 1 or 2 used in an absorbent material together with a hydrophilic fiber.

Item 4. The water-absorbent resin according to item 1 or 2 used for an absorbent article including a liquid-permeable sheet and a liquid-impermeable sheet.

Advantages of the Invention

The present invention can provide a water-absorbent resin which is capable of giving an absorbent material improved gel-shape stability and which has more excellent water-absorption capacity.

EMBODIMENTS OF THE INVENTION

1. Water-Absorbent Resin

A water-absorbent resin of the present invention is a polymer of a water-soluble ethylenically unsaturated monomer, and has the following properties (1) and (2).
(1) a disintegration amount at 20-fold swelling is 30% by mass or less; and
(2) a solubility in physiological saline is 25% by mass or less.
(Determination Method for Disintegration Amount at 20-Fold Swelling)

5 g of the water-absorbent resin is added to 100 g of physiological saline to allow the water-absorbent resin to absorb the physiological saline, thereby obtaining a gel. The obtained gel is divided approximately equally into five portions, and these portions are introduced respectively into cylindrical molds having a length of 3.6 cm and a radius of 2.8 cm and molded. The masses of the five molded cylindrical gels are measured. The heaviest and the lightest of the five gels are removed, and the remaining three gels are used as samples. A mass Wa (g) of each sample is measured. Each weighed sample is placed on the uppermost sieve of a combination of JIS standard sieves having a mesh size of 5.6 mm and a receptacle in this order and shaken for 10 minutes using a Ro-Tap shaker (rotation speed, 290 rpm; number of taps, 165 rpm). A mass Wb (g) of the gel which has passed through the sieves is measured. The disintegration amount of each sample is calculated using the following equation:

Disintegration amount of sample (%)=$Wb(g)/Wa(g) \times 100$.

An average of the disintegration amounts for three samples to be measured is regarded as the disintegration amount at 20-fold swelling of the water-absorbent resin.

The water-absorbent resin of the present invention having such a configuration is capable of giving an absorbent material improved gel-shape stability and has more excellent water-absorption capacity. When the water-absorbent resin of the present invention having such characteristics is used for a hygienic material, even if compression or a shearing force is applied due to the motion of a wearer, the water-absorbent resin can suppress deformation of an absorbent material and prevent cracking or uneven distribution. Furthermore, the water-absorbent resin can prevent diaper rash caused by a dissolved component eluted from the water-absorbent resin. Thus, the water-absorbent resin of the present invention can be suitably used for an absorbent material and an absorbent article for various applications. Especially, the water-absorbent resin of the present invention can be used suitably for a hygienic material such as a disposable diaper. The water-absorbent resin of the present invention will be hereinafter described in detail.

In the water-absorbent resin of the present invention, it suffices that (1) the disintegration amount at 20-fold swelling is 30% by mass or less, and the disintegration amount at 20-fold swelling is preferably 28% by mass or less, more preferably 26% by mass or less, and still more preferably 15% or less from the viewpoint of exhibiting more excellent water-absorption capacity while further improving the gel-shape stability of the absorbent material. The disintegration amount at 20-fold swelling is 0% by mass or more.

The disintegration amount at 20-fold swelling of the water-absorbent resin is a value measured by the above-mentioned method and, more specifically, is measured by the method described in the examples.

In the water-absorbent resin of the present invention, it suffices that (2) the solubility in physiological saline is 25% by mass or less, and the solubility in physiological saline is preferably 23% by mass or less, more preferably 21% by mass or less, and still more preferably 20% or less from the viewpoint of exhibiting more excellent water-absorption capacity while further improving the gel-shape stability of the absorbent material. The solubility in physiological saline is 0% by mass or more, and usually 5% by mass or more. Here, the expression "solubility in physiological saline" refers to an amount (percentage) of a low molecular weight polymer and oligomer flowing out of the water-absorbent resin together with the physiological saline when the water-absorbent resin absorbs the physiological saline to be swollen. If the solubility is high, the polymer and oligomer that have flowed out of the water-absorbent resin may cause diaper rash due to contact with the skin of a wearer of a disposable diaper.

The solubility in physiological saline is measured by the method described in the examples.

A median particle diameter of the water-absorbent resin of the present invention is not particularly limited, but for example, 200 μm to 600 μm, preferably 250 μm to 550 μm, and more preferably 300 μm to 500 μm. The median particle diameter of the water-absorbent resin can be measured using JIS standard sieves. More specifically, the median particle diameter represents a value as measured using the method described in the Examples.

Examples of shapes of the water-absorbent resin of the present invention include a substantially spherical shape, a shape in which particles having a substantially spherical shape are aggregated, a crushed indefinite shape, a shape in which particles having a crushed indefinite shape are aggregated, and a flat shape. Through the use of reversed phase suspension polymerization or spray droplet polymerization, a water-absorbent resin having a substantially spherical particle shape, such as a spherical or elliptical shape, or a shape in which single particles having a substantially spherical shape are aggregated, can be produced. Through the use of aqueous solution polymerization, a water-absorbent resin having a crushed indefinite shape or a shape in which particles having a crushed indefinite shape are aggregated can be produced.

The water-absorbent resin of the present invention may contain additives suitable for its purpose. Examples of such additives include inorganic powders, surfactants, oxidizing agents, reducing agents, metal chelating agents, radical chain inhibitors, antioxidants, anti-bacterial agents, and deodorizers. For example, when 0.05 to 5 parts by mass of amorphous silica as an inorganic powder is added to 100 parts by mass of the water-absorbent resin, the flowability of the water-absorbent resin can be improved.

2. Method for Producing Water-Absorbent Resin

The water-absorbent resin of the present invention can be produced by polymerizing a water-soluble ethylenically unsaturated monomer.

To polymerize the water-soluble ethylenically unsaturated monomer, a representative polymerization method such as aqueous solution polymerization, emulsion polymerization, or reversed phase suspension polymerization is used. In the aqueous solution polymerization method, polymerization is carried out by heating a water-soluble ethylenically unsaturated monomer aqueous solution while stirring it as necessary. In reversed phase suspension polymerization, polymerization is performed by heating the water-soluble ethylenically unsaturated monomer with stirring in a hydrocarbon dispersion medium. In the present invention, reversed phase suspension polymerization is preferred from the viewpoint of allowing the polymerization reaction to be precisely controlled, and a wide range of particle diameters to be controlled.

One exemplary method for producing the water-absorbent resin according to the present invention will be hereinafter described. Examples of methods for producing the water-absorbent resin include a method for producing the water-absorbent resin by performing reversed phase suspension polymerization of the water-soluble ethylenically unsaturated monomer in a hydrocarbon dispersion medium, the method including the steps of: performing the polymerization in the presence of an internal-crosslinking agent and a radical polymerization initiator; and post-crosslinking the hydrous gel having an internal crosslinking structure obtained by the polymerization in the presence of a post-crosslinking agent.

<Polymerization Step>

[Water-Soluble Ethylenically Unsaturated Monomer]

Examples of the water-soluble ethylenically unsaturated monomer include (meth)acrylic acid ("acry" and "methacry" are herein collectively referred to as "(meth)acry"; the same applies below) and salts thereof; 2-(meth)acrylamido-2-methylpropanesulfonic acid and salts thereof; nonionic monomers such as (meth)acrylamide, N,N-dimethyl(meth)acrylamide, 2-hydroxyethyl(meth)acrylate, N-methylol (meth)acrylamide, and polyethylene glycol mono(meth)acrylate: and amino group-containing unsaturated monomers such as N,N-diethylaminoethyl(meth)acrylate N,N-diethylaminopropyl(meth)acrylate, and diethylaminopropyl(meth)acrylamide, as well as quaternary compounds thereof. Preferred among these water-soluble ethylenically unsaturated monomers are (meth)acrylic acid and salts thereof, (meth)acrylamide, and N,N-dimethyl(meth)acrylamide, and more preferred are (meth)acrylic acid and salts thereof, from the viewpoint of being readily industrially available. These water-soluble ethylenically unsaturated monomers may be used alone or in combination of two or more.

Among these water-soluble ethylenically unsaturated monomers, acrylic acid and salts thereof are widely used as raw materials of water-absorbent resins. Copolymers of acrylic acid and salts thereof with other water-soluble ethylenically unsaturated monomers as mentioned above may also be used. In this case, an acrylic acid and a salt thereof as a main water-soluble ethylenically unsaturated monomer is preferably used in an amount of 70 to 100 mol % based on the total amount of water-soluble ethylenically unsaturated monomers.

The water-soluble ethylenically unsaturated monomer is preferably dispersed as an aqueous solution in a hydrocarbon dispersion medium, and then subjected to reversed phase suspension polymerization. When the water-soluble ethylenically unsaturated monomer is in the form of an aqueous solution, the dispersion efficiency in the hydrocarbon dispersion medium can be increased. The concentration of the water-soluble ethylenically unsaturated monomer in the aqueous solution is preferably in the range of 20% by mass to not more than the saturation concentration. The concentration of the water-soluble ethylenically unsaturated monomer is more preferably 55% by mass or less, still more preferably 50% by mass or less, and even more preferably 45% by mass or less. On the other hand, the concentration of the water-soluble ethylenically unsaturated monomer is more preferably 25% by mass or more, still more preferably 28% by mass or more, and even more preferably 30% by mass or more.

When the water-soluble ethylenically unsaturated monomer has an acid group such as (meth)acrylic acid or 2-(meth) acrylamido-2-methylpropanesulfonic acid, the acid group may be neutralized with an alkaline neutralizing agent, as required, before use. Examples of such alkaline neutralizing agents include alkali metal salts such as sodium hydroxide, sodium carbonate, sodium hydrogen carbonate, potassium hydroxide, and potassium carbonate; and ammonia. These alkaline neutralizing agents may be used in the form of aqueous solutions to facilitate the neutralization operation. The above-mentioned alkaline neutralizing agents may be used alone or in combination of two or more.

The degree of neutralization of the water-soluble ethylenically unsaturated monomer with an alkaline neutralizing agent, calculated as the degree of neutralization of all acid groups in the water-soluble ethylenically unsaturated monomer, is preferably 10 to 100 mol %, more preferably 30 to 90 mol %, still more preferably 40 to 85 mol %, and even more preferably 50 to 80 mol %.

[Internal-Crosslinking Agent]

Examples of the internal-crosslinking agent include those that can crosslink the polymer of the water-soluble ethylenically unsaturated monomer to be used, for example: unsaturated polyesters obtained by reacting polyols such as diols and triols, e.g., (poly)ethylene glycol ["(poly)" means both cases with and without the prefix "poly"; the same applies below], (poly)propylene glycol, 1,4-butanediol, trimethylolpropane, and (poly)glycerin, with unsaturated acids such as (meth)acrylic acid, maleic acid, and fumaric acid; bisacrylamides such as N,N-methylenebisacrylamide; di or tri(meth)acrylic acid esters obtained by reacting polyepoxides with (meth)acrylic acid; carbamyl di(meth)acrylates obtained by reacting polyisocyanates such as tolylene diisocyanate and hexamethylene diisocyanate with hydroxyethyl (meth)acrylate: compounds having two or more polymerizable unsaturated groups such as allylated starch, allylated cellulose, diallyl phthalate, N,N',N"-triallylisocyanate, and divinylbenzene; polyglycidyl compounds such as diglycidyl compounds and triglycidyl compounds, e.g., (poly)ethylene glycol diglycidyl ether, (poly)propylene glycol diglycidyl ether, and (poly)glycerin diglycidyl ether; epihalohydrin compounds such as epichlorohydrin, epibromohydrin, and α-methylepichlorohydrin; compounds having two or more reactive functional groups such as isocyanate compounds, e.g., 2,4-tolylene diisocyanate and hexamethylene diisocyanate; and oxetane compounds such as 3-methyl-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol. Among these internal-crosslinking agents, polyglycidyl compounds are preferably used, diglycidyl ether compounds are more preferably used, and (poly)ethylene glycol diglycidyl ether, (poly)propylene glycol diglycidyl ether, and (poly)glycerin diglycidyl ether are still more preferably used. These internal-crosslinking agents may be used alone or in combination of two or more.

The amount of the internal-crosslinking agent to be used is preferably 0.000001 to 0.02 mol, more preferably 0.00001 to 0.01 mol, and still more preferably 0.00001 to 0.005 mol, per mole of the water-soluble ethylenically unsaturated monomer.

[Hydrocarbon Dispersion Medium]

Examples of the hydrocarbon dispersion medium include $C_{6-8}$ aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. Among these hydrocarbon dispersion media, n-hexane, n-heptane, and cyclohexane, which are readily industrially available, stable in quality, and inexpensive, are particularly suitably used. These hydrocarbon dispersion media may be used alone or in combination of two or more. Examples of mixtures of hydrocarbon dispersion media include commercially available products such as Exxsol Heptane (from Exxon Mobil Corporation: containing 75 to 85% by mass of heptane and its isomeric hydrocarbons). The use of such a commercially available product also leads to favorable results.

The amount of the hydrocarbon dispersion medium to be used is preferably 100 to 1500 parts by mass, and more preferably 200 to 1400 parts by mass, per 100 parts by mass of the water-soluble ethylenically unsaturated monomer subjected to first-stage polymerization, from the viewpoint of homogeneously dispersing the water-soluble ethylenically unsaturated monomer, and facilitating control of the polymerization temperature. As described below, reversed phase suspension polymerization is performed in a single stage or two or more multiple stages. The first-stage polymerization as mentioned above refers to the first-stage polymerization reaction in single-stage polymerization or multistage polymerization (the same applies below).

[Dispersion Stabilizer]

(Surfactant)

In reversed phase suspension polymerization, a dispersion stabilizer may be used to improve the dispersion stability of the water-soluble ethylenically unsaturated monomer in the hydrocarbon dispersion medium. A surfactant may be used as such a dispersion stabilizer.

Examples of the surfactant include sucrose fatty acid esters, polyglycerin fatty acid esters, sorbitan fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde condensate polyoxyethylene ethers, polyoxyethylene-polyoxypropylene block copolymers, polyoxyethylene polyoxypropyl alkyl ethers, polyethylene glycol fatty acid esters, alkyl glucosides. N-alkyl glyconamides, polyoxyethylene fatty acid amides, polyoxyethylene alkylamines, polyoxyethylene alkyl ether phosphates, and polyoxyethylene alkyl allyl ether phosphates. Among these surfactants, sorbitan fatty acid esters, polyglycerin fatty acid esters, and sucrose fatty acid esters, are particularly preferably used, from the viewpoint of dispersion stability of the monomer. These surfactants may be used alone or in combination of two or more.

The amount of the surfactant to be used is preferably 0.1 to 30 parts by mass, and more preferably 0.3 to 20 parts by mass, per 100 parts by mass of the water-soluble ethylenically unsaturated monomer subjected to the first-stage polymerization.

(Polymeric Dispersion Agent)

A polymeric dispersion agent may be used in combination with the above-described surfactant, as a dispersion stabilizer to be used in reversed phase suspension polymerization.

Examples of the polymeric dispersion agent include maleic anhydride modified polyethylene, maleic anhydride modified polypropylene, maleic anhydride modified ethylene-propylene copolymers, maleic anhydride modified EPDM (ethylene-propylene-diene terpolymers), maleic anhydride modified polybutadiene, maleic anhydride-ethylene copolymers, maleic anhydride-propylene copolymers, maleic anhydride-ethylene-propylene copolymers, maleic anhydride-butadiene copolymers, polyethylene, polypropylene, ethylene-propylene copolymers, oxidized polyethylene, oxidized polypropylene, oxidized ethylene-propylene copolymers, ethylene-acrylic acid copolymers, ethyl cellulose, and ethyl hydroxyethyl cellulose. Among these polymeric dispersion agents, maleic anhydride modified polyethylene, maleic anhydride modified polypropylene, maleic anhydride modified ethylene-propylene copolymers, maleic anhydride-ethylene copolymers, maleic anhydride-propylene copolymers, maleic anhydride-ethylene-propylene copolymers, polyethylene, polypropylene, ethylene-propylene copolymers, oxidized polyethylene, oxidized polypropylene, and oxidized ethylene-propylene copolymers are particularly preferably used, from the viewpoint of dispersion stability of the monomer. These polymeric dispersion agents may be used alone or in combination of two or more.

The amount of the polymeric dispersion agent to be used is preferably 0.1 to 30 parts by mass, and more preferably 0.3 to 20 parts by mass, per 100 parts by mass of the water-soluble ethylenically unsaturated monomer subjected to the first-stage polymerization.

[Radical Polymerization Initiator]

As a radical polymerization initiator, a peroxide and an azo compound can be used, for example. Examples of peroxides include: persulfates such as potassium persulfate, ammonium persulfate, and sodium persulfate; and peroxides such as methyl ethyl ketone peroxide, methyl isobutyl ketone peroxide, di-t-butyl peroxide, t-butylcumyl peroxide, t-butyl peroxyacetate, t-butyl peroxyisobutyrate, t-butyl peroxypivalate, and hydrogen peroxide. Among these peroxides, potassium persulfate, ammonium persulfate, sodium persulfate, and hydrogen peroxide are preferably used, and further, persulfates such as potassium persulfate, ammonium persulfate, and sodium persulfate are more preferably used. Examples of azo compounds include 1-{(1-cyano-1-methylethyl)azo}formamide, 2,2'-azobis[2-(N-phenylamidino)propane]dihydrochloride, 2,2'-azobis{2-[N-(4-chlorophenyl) amidino]propane}dihydrochloride, 2,2'-azobis(2-[N-(4-hydroxyphenyl)amidino]propane)dihydrochloride, 2,2'-azobis[2-(N-benzylamidino)propane]dihydrochloride, 2,2'-azobis[2-(N-allylamidino)propane]dihydrochloride, 2,2'-azobis(2-amidinopropane)dihydrochloride, 2,2'-azobis{2-

[N-(2-hydroxyethyl)amidino]propane}dihydrochloride, 2,2'-azobis[2-(5-methyl-2-imidazolin-2-yl)propane]dihydrochloride, 2,2'-azobis[2-(2-imidazolin-2-yl)propane]dihydrochloride, 2,2'-azobis[2-(4,5,6,7-tetrahydro-H-1,3-diazepin-2-yl)propane]dihydrochloride, 2,2'-azobis[2-(5-hydroxy-3,4,5,6-tetrahydropyrimidin-2-yl)propane] dihydrochloride, 2,2'-azobis{2-[1-(2-hydroxyethyl)-2-imidazolin-2-yl]propane}dihydrochloride, 2,2'-azobis[2-(2-imidazolin-2-yl)propane], 2,2'-azobis(2-methyl-N-[1,1-bis (hydroxymethyl)-2-hydroxyethyl]propionamide), 2,2'-azobis(2-methyl-N-[1,1-bis(hydroxymethyl)ethyl] propionamide), 2,2'-azobis[2-methyl-N-(2-hydroxyethyl) propionamide], 2,2'-azobis(2-methylpropionamide) dihydrochloride, 4,4'-azobis-4-cyanovaleric acid, 2,2'-azobis[2-(hydroxymethyl)propionitrile], 2,2'-azobis[2-(2-imidazolin-2-yl)propane]disulfate dihydrate, 2,2'-azobis[N-(2-carboxyethyl)-2-methylpropioneamidine]tetrahydrate, and 2,2'-azobis[2-methyl-N-(2-hydroxyethyl)propionamide]. Of these, an azo compound such as 2,2'-azobis(2-amidinopropane)dihydrochloride, 2,2'-azobis{2-[1-(2-hydroxyethyl)-2-imidazolin-2-yl]propane}dihydrochloride, 2,2'-azobis[N-(2-carboxyethyl)-2-methylpropioneamidine] tetrahydrate, and the like, are preferable. Preferred among these radical polymerization initiators are potassium persulfate, ammonium persulfate, sodium persulfate, and 2,2'-azobis(2-amidinopropane) dihydrochloride, from the viewpoint of being readily available and easy to handle. These radical polymerization initiators may be used alone or in combination of two or more. In particular, when the radical polymerization initiators are used in combination of two or more, an azo compound and persulfates are preferable.

The above-mentioned radical polymerization initiators may also be used in combination with reducing agents such as sodium sulfite, sodium hydrogensulfite, ferrous sulfate, and L-ascorbic acid to be used as redox polymerization initiators.

The amount of the radical polymerization initiator to be used may be, for example, 0.00005 to 0.01 mol per mole of the water-soluble ethylenically unsaturated monomer, although not limited thereto. The use of the radical polymerization initiator in the above-defined range of amounts can avoid the occurrence of an abrupt polymerization reaction, and can complete the polymerization reaction in an appropriate time.

[Other Components]

In the method for producing the water-absorbent resin, other components may be added, as desired, to the aqueous solution containing the water-soluble ethylenically unsaturated monomer to be subjected to reversed phase suspension polymerization. Various additives such as thickeners and chain transfer agents may be added as other components.

[Reversed Phase Suspension Polymerization]

To perform reversed phase suspension polymerization, for example, the aqueous monomer solution containing the water-soluble ethylenically unsaturated monomer is added and dispersed in a hydrocarbon dispersion medium, in the presence of a dispersion stabilizer. Here, so long as the dispersion stabilizer (a surfactant or a polymeric dispersion agent) is added before the beginning of the polymerization reaction, it may be added either before or after the aqueous monomer solution is added.

From the viewpoint of readily reducing the amount of remaining hydrocarbon dispersion medium in the resulting water-absorbent resin, it is preferred to disperse the aqueous monomer solution in the hydrocarbon dispersion medium in which a polymeric dispersion agent is dispersed, followed by dispersing a surfactant therein, and then perform polymerization.

The reversed phase suspension polymerization can be performed in a single stage or two or more multiple stages. From the viewpoint of enhancing productivity, reversed phase suspension polymerization is preferably performed in two or three stages.

Reversed phase suspension polymerization with two or more multiple stages may be performed as follows: the first-stage reversed phase suspension polymerization is performed; subsequently, a water-soluble ethylenically unsaturated monomer is added to the reaction mixture obtained by the first-stage polymerization reaction and mixed, and reversed phase suspension polymerization in the second and subsequent stages is performed in the same manner as in the first stage. In reversed phase suspension polymerization in each of the second and subsequent stages, in addition to the water-soluble ethylenically unsaturated monomer, an internal-crosslinking agent and the above-described radical polymerization initiator are preferably added within the above-described range of molar ratios of each of the components relative to the water-soluble ethylenically unsaturated monomer, based on the amount of the water-soluble ethylenically unsaturated monomer added during reversed phase suspension polymerization in each of the second and subsequent stages.

The reaction temperature during the polymerization reaction is preferably 20 to 110° C., and more preferably 40 to 90° C., from the viewpoint of allowing the polymerization to proceed quickly to reduce the polymerization time for improved economical efficiency, and readily removing the heat of polymerization to perform a smooth reaction. The reaction time is preferably 0.5 to 4 hours.

<Post-Crosslinking Step>

The water-absorbent resin according to the present invention may be obtained by post-crosslinking the hydrous gel having an internally crosslinked structure obtained by polymerizing the water-soluble ethylenically unsaturated monomer, using a post-crosslinking agent (post-crosslinking reaction). The post-crosslinking reaction is preferably preformed in the presence of a post-crosslinking agent, after the polymerization of the water-soluble ethylenically unsaturated monomer. When the hydrous gel having an internally crosslinked structure is thus subjected to the post-crosslinking reaction after the polymerization, a water-absorbent resin can be achieved in which the crosslinking density in the vicinity of the surface has been increased to improve various kinds of performance such as the water-absorption capacity under a load.

Examples of the post-crosslinking agent include compounds having two or more reactive functional groups, for example: polyols such as ethylene glycol, propylene glycol, 1,4-butanediol, trimethylolpropane, glycerin, polyoxyethylene glycol, polyoxypropylene glycol, and polyglycerin: polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol diglycidyl ether, and polyglycerol polyglycidyl ether; haloepoxy compounds such as epichlorohydrin, epibromohydrin, and α-methylepichlorohydrin; isocyanate compounds such as 2,4-tolylene diisocyanate and hexamethylene diisocyanate; oxetane compounds such as 3-methy-3-oxetanemethanol, 3-ethyl-3-oxetanemethanol, 3-butyl-3-oxetanemethanol, 3-methyl-3-oxetaneethanol, 3-ethyl-3-oxetaneethanol, and 3-butyl-3-oxetaneethanol: oxazoline compounds such as 1,2-ethylenebisoxazoline; carbonate compounds such as ethylene carbonate; and hydroxyalkylamide compounds such as bis[N,N-di(pβ-hydroxyethyl)]adipamide. Preferred among these post-crosslinking agents are polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol diglycidyl ether, and polyglycerol polyglycidyl ether. These post-crosslinking agents may be used alone or in combination of two or more.

The amount of the post-crosslinking agent to be used is preferably 0.00001 to 0.01 mol, more preferably 0.00005 to 0.005 mol, and still more preferably 0.0001 to 0.002 mol, per mole of the water-soluble ethylenically unsaturated monomer subjected to polymerization. In the case of multistage reversed-phase suspension polymerization by two or more stages, the amount of the water-soluble ethylenically unsaturated monomer, which is the basis of the amount of the post-crosslinking agent to be used, is the total amount of the water-soluble ethylenically unsaturated monomer used in each stage.

The post-crosslinking agent may be added as is or as an aqueous solution. As required, a solution of the post-crosslinking agent in a hydrophilic organic solvent may be added. Examples of such hydrophilic organic solvents include lower alcohols such as methyl alcohol, ethyl alcohol, n-propyl alcohol, and isopropyl alcohol; ketones such as acetone and methyl ethyl ketone; ethers such as diethyl ether, dioxane, and tetrahydrofuran; amides such as N,N-dimethylformamide; and sulfoxides such as dimethylsulfoxide. These hydrophilic organic solvents may be used alone, in combination of two or more, or as a mixture with water.

The post-crosslinking agent may be added after the polymerization reaction of the water-soluble ethylenically unsaturated monomer is substantially completed. The post-crosslinking agent is preferably added in the presence of 1 to 400 parts by mass of water, more preferably 5 to 200 parts by mass of water, still more preferably 10 to 100 parts by mass of water, and even more preferably 20 to 60 parts by mass of water, per 100 parts by mass of the water-soluble ethylenically unsaturated monomer. The amount of water herein refers to the total amount of the water contained in the reaction system and the water that is used, as required, during the addition of the post-crosslinking agent.

The reaction temperature during the post-crosslinking reaction is preferably 50 to 250° C., more preferably 60 to 180° C., still more preferably 60 to 140° C., and even more preferably 70 to 120° C. The reaction time of the post-crosslinking reaction is preferably 1 to 300 minutes, and more preferably 5 to 200 minutes.

<Drying Step>

The method for producing the water-absorbent resin of the present invention may include, after performing reversed phase suspension polymerization as described above, a drying step of adding external energy such as heat to remove the water, hydrocarbon dispersion medium, and the like by distillation. To remove the water in the hydrous gel after reversed phase suspension polymerization, the system in which the hydrous gel is dispersed in the hydrocarbon dispersion medium is heated to distill the water and the hydrocarbon dispersion medium out of the system by azeotropic distillation. Here, if the distilled hydrocarbon dispersion medium only is returned into the system, continuous azeotropic distillation can be performed. In this case, the temperature within the system during drying is maintained at a temperature not higher than the azeotropic temperature with the hydrocarbon dispersion medium, which is preferable from the viewpoint of inhibiting deterioration of the resin. Subsequently, the water and the hydrocarbon dispersion medium are distilled off to obtain particles of the water-absorbent resin. By controlling the treatment conditions for the drying step after the polymerization to adjust the amount of water to be removed, various kinds of performance of the resulting water-absorbent resin can be controlled.

In the drying step, the drying treatment may be performed under atmospheric pressure or reduced pressure. The drying treatment may also be performed in a stream of nitrogen or the like, from the viewpoint of enhancing the drying efficiency. When the drying treatment is performed under atmospheric pressure, the drying temperature is preferably 70 to 250° C., more preferably 80 to 180° C., still more preferably 80 to 140° C., and even more preferably 90 to 130° C. When the drying treatment is performed under reduced pressure, the drying temperature is preferably 40 to 160° C., and more preferably 50 to 110° C.

When the post-crosslinking step with a post-crosslinking agent is performed after the polymerization of the monomer by reversed phase suspension polymerization, the drying step by distillation is preferably performed as described above, after the completion of the post-crosslinking step. Alternatively, the post-crosslinking step and the drying step may be performed simultaneously.

Furthermore, various additives such as chelating agents, reducing agents, oxidizing agents, anti-bacterial agents, and deodorizers may be added, as required, to the water-absorbent resin, after polymerization, during drying, or after drying.

3. Absorbent Material and Absorbent Article

The water-absorbent resin according to the present invention constitutes an absorbent material to be used for hygienic materials such as sanitary items and disposable diapers, and is suitably used for an absorbent article including the absorbent material.

Here, the absorbent material including the water-absorbent resin is composed of, for example, the water-absorbent resin and hydrophilic fibers. Examples of structures of the absorbent material include a mixed dispersion obtained by mixing the water-absorbent resin and hydrophilic fibers to give a homogeneous composition; a sandwich structure in which the water-absorbent resin is sandwiched between layered hydrophilic fibers; and a structure in which the water-absorbent resin and hydrophilic fibers are wrapped in tissue paper. The absorbent material may also contain other components such as thermally fusible synthetic fibers for enhancing the shape retention properties of the absorbent material, a hot melt adhesive, and an adhesive binder such as an adhesive emulsion.

The content of the water-absorbent resin in the absorbent material is preferably 5 to 100% by mass, more preferably 20 to 95% by mass, and still more preferably 30 to 90% by mass. From the viewpoint of reducing the thickness of the absorbent material, the content of the water-absorbent resin in the absorbent material is preferably 50% by mass or more.

Examples of hydrophilic fibers include cellulose fibers such as cotton-like pulp made from wood, mechanical pulp, chemical pulp, and semi-chemical pulp; artificial cellulose fibers such as rayon and acetate; and fibers made of synthetic resins such as hydrophilized polyamide, polyester, and polyolefin.

As described above, since the water-absorbent resin of the present invention is capable of giving the absorbent material improved gel-shape stability and has more excellent water-absorption capacity, the water-absorbent resin can be suitably used for an absorbent material having a low proportion of hydrophilic fibers.

The absorbent material including the water-absorbent resin can be held between a liquid-permeable sheet (top sheet) that allows a liquid to pass through and a liquid-impermeable sheet (back sheet) that does not allow a liquid to pass through, to constitute an absorbent article. The liquid-permeable sheet is positioned on the side of the absorbent article that is brought into contact with the body, and the liquid-impermeable sheet is positioned opposite to the side that is brought into contact with the body.

Examples of the liquid-permeable sheet include air-through, spunbond, chemical bond, or needle punch non-woven fabrics made of fibers of polyethylene, polypropylene, polyester, or the like, and porous synthetic resin sheets. Examples of the liquid-impermeable sheet include synthetic resin films made of resins such as polyethylene, polypropylene, and polyvinyl chloride.

As described above, since the water-absorbent resin of the present invention is capable of giving the absorbent material improved gel-shape stability and has more excellent water-absorption capacity, when the water-absorbent resin of the present invention is used for an absorbent material having a low proportion of hydrophilic fibers, a thin absorbent article (for example, an absorbent article in which the thickness of the absorbent material is preferably 5 mm or less, more preferably 3 mm or less) can be constituted.

EXAMPLES

Hereinafter, the present invention will be described in detail with reference to examples and comparative examples. However, the present invention is not limited to the examples.

For the water-absorbent resin obtained in each example and comparative example, the disintegration amount at 20-fold swelling, the solubility in physiological saline, the median particle diameter, a physiological-saline absorption capacity under a load, and presence or absence of reduction in gel height with a lapse of time were measured by the following respective methods.

<Disintegration Amount at 20-Fold Swelling>

100 g of a 0.9% by mass aqueous solution of sodium chloride (physiological saline) was weighed out into a 100-ml beaker, and 5 g of the water-absorbent resin was dispersed therein with stirring at 600 rpm, so as not to unswollen lumps. After the water-absorbent resin absorbed water and the stirring was stopped, the mixture was allowed to stand for 5 minutes. Thereafter, the swollen water-absorbent resin was taken out in a 500-m beaker, the hardened water-absorbent resin was loosened with a spatula, and all the taken out water-absorbent resins were uniformly put into a push mold (makunouchi push mold from Nishiki Kasei Co., Ltd. (in which five cylindrical molds having a length of 3.6 cm and a radius of 2.8 cm are continuously provided)). A 5 kg weight was placed from above a lid of the push mold, and after leaving for 10 minutes, five lumps of the water-absorbent resin pressed into a cylindrical shape was taken out from the push mold with a spatula. The mass of each lump was measured. The heaviest and the lightest of the five lumps were removed, and the remaining three lumps were used as measurement samples. The mass Wa (g) of each sample was measured. Each weighed sample was placed on the uppermost sieve of a combination of JIS standard sieves having a mesh size of 5.6 mm (sieve inside diameter, 20 cmφ) and a receptacle in this order and shaken for 10 minutes using a Ro-Tap shaker (from iida-seisakusho Japan Corporation, rotation speed, 290 rpm; number of taps, 165 rpm). The mass Wb (g) of the gel which has passed through the sieves was measured. The measurement was performed three times, and the average value was regarded as the disintegration amount at 20-fold swelling. The disintegration amount of each sample was calculated using the following equation. The average of the disintegration amounts for three samples to be measured was regarded as the disintegration amount at 20-fold swelling.

$$\text{Disintegration amount of sample (\%)} = Wb(g)/Wa(g) \times 100$$

<Solubility in Physiological Saline>

500±0.1 g of a 0.9% by mass aqueous solution of sodium chloride (physiological saline) was weighed out into a 500-ml beaker, and then a magnetic stirrer bar (8 mmφ×30 mm, having no rings) was put in. Then, the beaker was put on a magnetic stirrer (from Koike Precision Instruments (KPI); product number: Mighty Stirrer M-16GM×6). Subsequently, the rotation of the magnetic stirrer bar was adjusted to 600 rpm, and the bottom of the vortex generated by the rotation of the magnetic stirrer bar was adjusted so that it was located near the upper portion of the magnetic stirrer bar. Subsequently, 2.0±0.002 g of water-absorbent resin was dispersed by being quickly added between the center portion of the vortex in the beaker and the sidewall of the beaker, followed by stirring for 3 hours. The water-absorbent resin dispersion after stirring for 3 hours was filtered through a standard sieve (mesh size, 75 μm) and the resulting filtrate was further subjected to filtration under reduced pressure using Kiriyama-rohto (filter paper No. 6). 80±0.1 g of the resulting filtrate was weighed in a 100-mL beaker having a constant weight and dried in a hot air oven (from ADVANTEC Co., Ltd.) set at 140° C. until it reached a constant weight. Thereafter, the mass Wc (g) of the solids content of the filtrate was measured. On the other hand, the procedure described above was performed without using the water-absorbent resin to measure the mass Wd (g) of the solids content of the filtrate, and the solubility in physiological saline was calculated by the following equation:

$$\text{Solubility in physiological saline (mass \%)} = [[(Wc-Wd) \times (500/80)]/2] \times 100$$

<Median Particle Diameter>

0.1 g of amorphous silica (Degussa Japan, Sipemat 200) was mixed as a lubricant with 50 g of a water-absorbent resin. The mixture was allowed to pass through a JIS standard sieve having a mesh size of 250 μm. When the residual amount on the sieve was less than 50% by mass of the mixture, the median particle diameter was measured using the following combination <A> of sieves. When the residual amount was 50% by mass or more, the median particle diameter was measured using the following combination <B> of sieves.

<A> JIS standard sieves having mesh sizes of 425 μm, 250 μm, 180 μm, 150 μm, 106 μm, 75 μm, and 45 μm, and a receptacle were combined in that order from the top.

<B> JIS standard sieves having mesh sizes of 850 μm, 600 μm, 500 μm, 425 μm, 300 μm, 250 μm, and 150 μm, and a receptacle were combined in that order from the top.

The water-absorbent resin was placed on the top sieve of the combined sieves, and shaken for 10 minutes with a Ro-Tap shaker to conduct classification. After the classification, the particle size distribution was determined by calculating the mass of the water-absorbent resin remaining on each sieve as the mass percentage relative to the total mass. With regard to this particle size distribution, the mass percentage of water-absorbent resin particles remaining on each sieve was integrated in descending order of particle diameter. Thereby, the relationship between the sieve mesh size and the integrated value of the mass percentage of the water-absorbent resin remaining on each sieve was plotted on logarithmic probability paper. The plots on the probability paper were connected with straight lines, and a particle diameter equivalent to 50% by mass of the integrated mass percentage was determined as the median particle diameter.

<Physiological-Saline Absorption Capacity Under Load>

Figure 1:
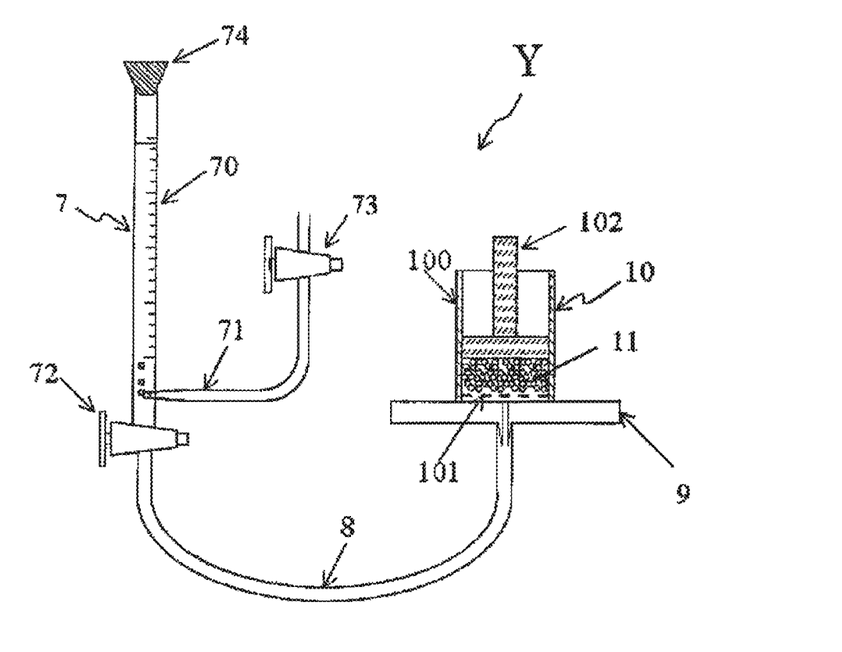
FIG. 1 is a schematic diagram showing a schematic configuration of an apparatus for measuring a physiological-saline absorption capacity under a load.

The physiological-saline absorption capacity under a load of a water-absorbent resin was measured by using a measurement apparatus Y whose schematic configuration is illustrated in FIG. 1. The measurement apparatus Y shown in FIG. 1 includes a burette section 7, a tube 8, a measuring board 9, and a measuring section 10 placed on the measuring board 9. The burette section 7 is connected to a rubber plug 74 on the top portion of a burette 70 and also connected to an air inlet tube 71 and a cock 72 at the bottom portion, and a cock 73 is placed at the end of the air inlet tube 71. The tube 8 is provided between the burette section 7 and the measuring board 9. The tube 8 has an inside diameter of 6 mm. A 2-mm-diameter hole is formed in the center of the measuring board 9, and the tube 8 is connected to the hole. The measuring section 10 has a cylinder 100 (made of acrylic resin), a nylon mesh 101 adhered to the bottom of the cylinder 40, and a weight 102. The cylinder 100 has an inside diameter of 20 mm. The mesh size of the nylon mesh 101 is 75 μm (200 mesh). At the time of the measurement, the water-absorbent resin 11 is uniformly distributed on the nylon mesh 101. The weight 102 has a diameter of 19 mm and a mass of 119.6 g. The weight is placed on the water-absorbent resin 11 so that a load of 4.14 kPa can be applied to the water-absorbent resin 11.

Next, the measurement procedure will be described. The measurements were taken indoors at 25° C. First, the cock 72 and the cock 73 at the burette section 7 were closed, a 0.9% by mass saline solution adjusted to 25° C. was poured from the top of the burette 70, and the top of the burette was plugged with the rubber plug 74. Thereafter, the cock 72 and the cock 73 at the burette section 7 were opened. Next, the height of the measuring board 9 was adjusted so that the water level of the 0.9% by mass saline solution flowing out from a lead tube port at the central section of the measuring board 9 is at the same height as an upper side of the measuring board 9.

Separately, 0.10 g of particles of the water-absorbent resin 11 were uniformly dispersed over the nylon mesh 101 in the cylinder 100, and the weight 102 was placed on the water-absorbent resin 11 to prepare the measuring section 10. Subsequently, the measuring section 10 was placed so that its center was aligned with the lead tube port at the central section of the measuring board 9.

The amount of reduced 0.9% by mass saline solution in the burette 1X) (i.e. the amount of 0.9% by mass saline solution absorbed by the water-absorbent resin 11) Wc (ml) was continuously measured from the time point when the water-absorbent resin 11 started to absorb water. The physiological-saline absorption capacity under the load of the water-absorbent resin 11 at 60 minutes after the start of water absorption was determined by the following equation:

Physiological-saline absorption capacity under load $(ml/g)=We/0.10$

The physiological-saline absorption capacity under a load is an index which shows the water-absorption capacity of the water-absorbent resin, and is preferably 15 (ml/g) or more and more preferably 20 (ml/g).

<Presence or Absence of Reduction in Gel Height with Lapse of Time>

The following 1-hour gel height Wf (mm) and 15-hours gel height Wg (mm) were compared to determine presence or absence of reduction in gel height with a lapse of time in the water-absorbent resin.

(1-Hour Gel Height)

500±0.1 g of a 0.9% by mass aqueous solution of sodium chloride (physiological saline) was poured into a 500-ml beaker, and then a magnetic stirrer bar (8 mmφ×30 mm, having no rings) was put in. Then, the beaker was put on a magnetic stirrer (from Koike Precision Instruments (KPI); product number: Mighty Stirrer M-16GM×6). Subsequently, the rotation of the magnetic stirrer bar was adjusted to 600 rpm, and the bottom of the vortex generated by the rotation of the magnetic stirrer bar was adjusted so that it was located near the upper portion of the magnetic stirrer bar. Thereafter, 2.0 g of the water-absorbent resin was added thereto and stirred for 1 hour. The stirring was stopped, and the mixture was allowed to stand for 15 minutes. Thereafter, the height Wf (mm) from a bottom surface of the beaker to the top of gel was measured. When the height of the gel changed with measurement positions, the height Wf (mm) was regarded as an average value of the highest value and the lowest value.

(15-Hours Gel Height)

500±0.1 g of a 0.9% by mass aqueous solution of sodium chloride (physiological saline) was poured into a 500-ml beaker, and then a magnetic stirrer bar (8 mmφ×30 mm, having no rings) was put in. Then, the beaker was put on a magnetic stirrer (from Koike Precision Instruments (KPI); product number: Mighty Stirrer M-16GM×6). Subsequently, the rotation of the magnetic stirrer bar was adjusted to 600 rpm, and the bottom of the vortex generated by the rotation of the magnetic stirrer bar was adjusted so that it was located near the upper portion of the magnetic stirrer bar. Thereafter, 2.0 g of the water-absorbent resin was added thereto and stirred for 15 hours. The stirring was stopped, and the mixture was allowed to stand for 15 minutes. Thereafter, the height Wg (mm) from a bottom surface of the beaker to the top of gel was measured. When the height of the gel changed with measurement positions, the height Wg (mm) was regarded as an average value of the highest value and the lowest value.

The presence or absence of reduction in gel height with a lapse of time (15-hours gel height to 1-hour gel height) is an index which shows the gel-shape stability of the absorbent material, and it is better not to reduce the gel height.

<Production of Water-Absorbent Resin>

Example 1

A cylindrical round-bottomed separable flask having an inside diameter of 100 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 500 ml of n-heptane, and then 0.80 g of a sucrose stearate (Ryoto sugar ester S-370 from Mitsubishi-Kagaku Foods Corporation) of HLB3 and 0.80 g of a maleic anhydride-modified ethylene-propylene copolymer (Hi-wax 1105A from Mitsui Chemicals, Inc.) were added thereto. The mixture was heated to 80° C. to dissolve the surfactant, and then cooled to 50° C.

Separately, 92.0 g (1.02 mol) of an 80% by mass aqueous solution of acrylic acid was placed in a 500-mL Erlenmeyer flask, and 153.2 g of a 20% by mass aqueous solution of sodium hydroxide was added dropwise with external cooling to accomplish 75 mol % neutralization. Then, 1.38 g of hydroxyethylcellulose (HEC AW-15F from Sumitomo Seika Chemicals Co. Ltd.) as a thickener, 0.092 g (0.000339 mol) of 2,2'-azobis(2-amidinopropane) dihydrochloride as a radical polymerization initiator, 0.018 g (0.0000681 mol) of potassium persulfate, and 0.0178 g (0.0000581 mol) of polyethylene glycol diglycidyl ether (EX-821 n=4 from Nagase ChemteX Corporation) as an internal-crosslinking agent were added and dissolved. As a result, an aqueous monomer solution was prepared.

The above-mentioned aqueous monomer solution was added to the above-mentioned separable flask and was kept at 40° C. for 30 minutes under replacement of the atmosphere in the system with nitrogen. Thereafter, the flask was immersed in a water bath kept at 70° C. to be heated and polymerization was carried out for 30 minutes, so that a slurry after polymerization was obtained.

Subsequently, the temperature was raised by using an oil bath at 125° C. and 115.5 g of water was removed to the outside of the system under reflux of n-heptane by azeotropic distillation of water and n-heptane, and then 4.60 g (0.000528 mol) of a 2% by mass aqueous solution of ethylene glycol diglycidyl ether was added as a post-crosslinking agent. The resulting mixture was kept at 80° C. for 2 hours and then dried by evaporating n-heptane, so that 97.0 g of a water-absorbent resin having a substantially spherical shape was obtained. Table 1 shows the measurement results of each property.

Example 2

The same operations as those of Example 1 were carried out except that the internal-crosslinking agent was changed to 0.0139 g (0.0000264 mol) of polyethylene glycol diglycidyl ether (EX-830, n=9 from Nagase ChemteX Corporation) and the amount of water to be removed during azeotropic distillation was changed to 116.22 g in Example 1, so that 93.5 g of a water-absorbent resin having a substantially spherical shape was obtained. Table 1 shows the measurement results of each property.

Example 3

The same operations as those of Example 1 were carried out except that the internal-crosslinking agent was changed to 0.029 g (0.0000264 mol) of polyethylene glycol diglycidyl ether (EX-861, n=22 from Nagase ChemteX Corporation) and the amount of water to be removed during azeotropic distillation was changed to 116.5 g in Example 1, so that 92.1 g of a water-absorbent resin having a substantially spherical shape was obtained. Table 1 shows the measurement results of each property.

Example 4

The same operations as those of Example 1 were carried out except that the internal-crosslinking agent was changed to 0.0081 g (0.0000264 mol) of polyethylene glycol diglycidyl ether (EX-821, n=4 from Nagase ChemteX Corporation) and the amount of water to be removed during azeotropic distillation was changed to 117.5 g in Example 1, so that 96.0 g of a water-absorbent resin having a substantially spherical shape was obtained. Table 1 shows the measurement results of each property.

Comparative Example 1

The same operations as those of Example 1 were carried out except that the internal-crosslinking agent was changed to 0.028 g (0.0000158 mol) of ethylene glycol diglycidyl ether and the amount of water to be removed during azeotropic distillation was changed to 112.9 g in Example 1, so that 112.1 g of a water-absorbent resin having a substantially spherical shape was obtained. Table 1 shows the measurement results of each property.

Comparative Example 2

A cylindrical round-bottomed separable flask having an inside diameter of 100 mm, and equipped with a reflux condenser, a dropping funnel, a nitrogen gas inlet tube, and a stirrer having stirring blades composed of two sets of four inclined paddle blades with a blade diameter of 50 mm was prepared. This flask was charged with 500 ml of n-heptane, and then 0.80 g of a sucrose stearate (Ryoto sugar ester S-370 from Mitsubishi-Kagaku Foods Corporation) of HLB3 was added thereto. The mixture was heated to 80° C. to dissolve the surfactant, and then cooled to 50° C.

Separately, 92.0 g (1.02 mol) of an 80% by mass aqueous solution of acrylic acid was placed in a 500-mL Erlenmeyer flask, and 153.2 g of a 20% by mass aqueous solution of sodium hydroxide was added dropwise with external cooling to accomplish 75 mol % neutralization. Then, 0.108 g of hydroxyethylcellulose (HEC AW-15F from Sumitomo Seika Chemicals Co. Ltd.) as a thickener, 0.092 g (0.000339 mol) of 2,2'-azobis(2-amidinopropane) dihydrochloride as a radical polymerization initiator, 0.018 g (0.0000681 mol) of potassium persulfate, 0.0046 g (0.0000264 mol) of ethylene glycol diglycidyl ether as an internal-crosslinking agent were added and dissolved. As a result, an aqueous monomer solution was prepared.

The above-mentioned first-stage aqueous monomer solution was added to the above-mentioned separable flask and was kept at 40° C. for 30 minutes under replacement of the atmosphere in the system with nitrogen. Thereafter, the flask was immersed in a water bath kept at 70° C. to be heated and polymerization was carried out, so that a slurry after first-stage polymerization was obtained.

Separately, 128.8 g (1.43 mol) of an 80% by mass aqueous solution of acrylic acid was placed in another 500-mL Erlenmeyer flask, and 158.9 g of a 27% by mass aqueous solution of sodium hydroxide was added dropwise with external cooling to accomplish 75 mol % neutralization. Then, 0.129 g (0.000475 mol) of 2,2'-azobis(2-amidinopropane) dihydrochloride as a radical polymerization initiator and 0.0116 g (0.0000666 mol) of ethylene glycol diglycidyl ether as an internal-crosslinking agent were added and dissolved. As a result, a second-stage aqueous monomer solution was prepared.

The above-mentioned slurry after polymerization was cooled to 23° C. and the second-stage aqueous monomer solution was added into the system and then the system was held for 30 minutes under replacement with nitrogen. The flask was immersed again in a water bath at 70° C. and the temperature was raised to perform polymerization, so that a slurry after second-stage polymerization was obtained.

Subsequently, the temperature was raised by using an oil bath at 125° C. and 261.7 g of water was removed to the outside of the system under reflux of n-heptane by azeotropically distillation of water and n-heptane, and then 4.42 g (0.000528 mol) of a 2% by mass aqueous solution of ethylene glycol diglycidyl ether was added as a post-crosslinking agent. The resulting mixture was kept at 80° C. for 2 hours and then dried by evaporating n-heptane, so that 230 g of a water-absorbent resin having a shape in which particles having a substantially spherical shape are aggregated was obtained. Table 1 shows the measurement results of each property.

Comparative Example 3

Comparative Example 3 was carried out with reference to an example of Japanese Patent No. 5143073. 670.0 g of a 37% aqueous solution of sodium acrylate and 102.0 g of acrylic acid were mixed to prepare a partially neutralized acrylic acid solution having 65 mol % neutralization. 772.0 g of the partially neutralized acrylic acid solution was mixed with 0.86 g of polyethylene glycol diacrylate (average unit numbers of polyethylene oxide: 9) and 220.0 g of water to prepare an aqueous monomer solution. The aqueous monomer solution was weighed in an amount of 745.5 g in a vat (made of stainless steel: diameter 188 mm, height 60 mm), and nitrogen was blown such that dissolved oxygen in the solution was 0.1 ppm or less.

Subsequently, the temperature of the above aqueous solution was adjusted to 18° C. under a nitrogen atmosphere, and then 1.19 g of a 5% aqueous solution of sodium persulfate, 1.19 g of a 5% aqueous solution of 2,2'-azobis(2-amidinopropane) hydrochloride, 1.13 g of 0.5% aqueous L-ascorbic acid solution, and 1.28 g of 0.35% aqueous hydrogen peroxide solution were sequentially added dropwise under stirring.

Polymerization started immediately after dropping of hydrogen peroxide, and after 9 minutes, the temperature of the monomer reached the peak temperature. The peak temperature was 86° C. Subsequently, the vat was immersed in a water bath at 80° C. and aged for 10 minutes.

The obtained transparent hydrous gel was crushed by a 1 L double-arm kneader and then dried at 180° C. for 30 minutes.

The dried product was pulverized by a pulverizer (rotor beater mill), and particles remaining on a sieve with a mesh size of 105 μm that passed through a sieve with a mesh size of 500 μm were classified to obtain a water-absorbent resin.

30.0 g of the water-absorbing rein obtained in the above production example was mixed with a composition liquid comprising 0.0015 g of ethylene glycol diglycidyl ether, 0.3 g of propylene glycol, 0.9 g of water, and 0.3 g of isopropyl alcohol and then heat-treated at 180° C. for 40 minutes to obtain 27.4 g of a water-absorbent resin having a crushed indefinite shape. Table 1 shows the measurement results of each property.

As is clear from the results shown in Table 1, the water-absorbent resins of Examples 1 to 4 in which the solubility in physiological saline is 25% by mass or less and the disintegration amount at 20-fold swelling is 30% by mass or less are capable of giving an absorbent material improved gel-shape stability, have a high physiological-saline absorption capacity under a load, and have excellent water-absorption capacity. On the other hand, in Comparative Examples 1 and 3, it can be seen that the disintegration amount at 20-fold swelling is large and the gel-shape stability of the absorbent material is poor. In Comparative Example 2, it can be seen that the solubility in physiological saline is high and a physiological-saline absorption capacity (water-absorption capacity) under a load is poor.

DESCRIPTION OF REFERENCE SIGNS

Y: Measurement apparatus of physiological-saline absorption capacity under load
7: Burette section
70: Burette
71: Air inlet tube
72: Cock
73: Cock
74: Rubber plug
8: Tube
9: Measuring board
10: Measuring section
100: Cylinder
101: Nylon mesh
102: Weight
11: Water-absorbent resin

The invention claimed is:

1. A water-absorbent resin, which is a polymer of a (meth)acrylic acid and/or a salt thereof, comprising properties (1) and (2):
   (1) wherein the disintegration amount of the water-absorbent resin at 20-fold swelling is 30% by mass or less; and
   (2) wherein the solubility of the water-absorbent resin in physiological saline is 25% by mass or less,
   wherein the disintegration amount at 20-fold swelling is determined by:
      adding the water-absorbent resin to physiological saline to allow the water absorbent resin to absorb the physiological saline, thereby obtaining a gel,
      dividing the gel into five approximately equal portions,
      introducing the portions into cylindrical molds to form molded cylindrical gels,
      measuring the masses of the molded cylindrical gels,
      removing the heaviest and the lightest of the gels,
      measuring a mass Wa (g) of each of the three remaining samples,

TABLE 1

|  |  | Disintegration amount at 20-fold swelling (%) | Solubility in physiological saline (%) | Median particle diameter (μm) | Physiological-saline absorption capacity under load (0.6 PSI) (mL/g) | Reduction in gel height with lapse of time (presence/absence) |
|---|---|---|---|---|---|---|
| Example | 1 | 29 | 9 | 430 | 32 | Absence (A) |
|  | 2 | 14 | 14 | 370 | 33 | A |
|  | 3 | 15 | 20 | 395 | 24 | A |
|  | 4 | 3 | 16 | 349 | 26 | A |
| Comparative Example | 1 | 51 | 10 | 346 | 30 | Presence (P) |
|  | 2 | 1 | 29 | 338 | 12 | A |
|  | 3 | 80 | 14 | 365 | 25 | P | placing each weighed sample on the uppermost sieve of a combination of JIS standard sieves having a mesh size of 5.6 mm and a receptacle in this order and shaken for 10 minutes using a Ro-Tap shaker (rotation speed, 290 rpm; number of taps, 165 rpm), measuring a mass Wb (g) of the gel which has passed through the sieves, wherein the disintegration amount of sample (%)=Wb (g)/Wa (g)×100 and wherein an average of the disintegration amounts for three samples to be measured is regarded as the disintegration amount at 20-fold swelling of the water-absorbent resin, wherein a median particle diameter of the water-absorbent resin is 200 μm to 430 μm.

2. The water-absorbent resin according to claim 1, wherein a median particle diameter is 300 μm to 430 μm.

3. An absorbent material comprising the water-absorbent resin according to claim 1 and a hydrophilic fiber.

4. An absorbent article comprising the water-absorbent resin according to claim 1 with a liquid-permeable sheet and a liquid-impermeable sheet.

5. An absorbent material comprising the water-absorbent resin according to claim 2 and a hydrophilic fiber.

6. An absorbent article comprising the water-absorbent resin according to claim 2 with a liquid-permeable sheet and a liquid-impermeable sheet.

* * * * *